United States Patent
Stinson

(10) Patent No.: US 6,926,733 B2
(45) Date of Patent: Aug. 9, 2005

(54) METHOD FOR ENHANCING SHEET OR TUBING METAL STENT RADIOPACITY

(75) Inventor: Jonathan Swift Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 241 days.

(21) Appl. No.: 09/920,998

(22) Filed: Aug. 2, 2001

(65) Prior Publication Data

US 2003/0028241 A1 Feb. 6, 2003

(51) Int. Cl.⁷ .................................................. A61F 2/06
(52) U.S. Cl. ...................................... 623/1.15; 623/1.34
(58) Field of Search ............................... 623/1.15, 1.34; 424/422–425; 264/642, 645, 656; 419/10–19; 427/2.24

(56) References Cited

U.S. PATENT DOCUMENTS

| | | | | |
|---|---|---|---|---|
| 5,498,227 A | * | 3/1996 | Mawad | 600/3 |
| 5,679,470 A | | 10/1997 | Mayer | 428/662 |
| 5,725,570 A | | 3/1998 | Heath | 623/1 |
| 5,725,572 A | | 3/1998 | Lam et al. | 623/1 |
| 5,733,326 A | | 3/1998 | Tomonto et al. | 623/1 |
| 5,916,263 A | * | 6/1999 | Goicoechea et al. | 623/1.11 |
| 5,972,027 A | * | 10/1999 | Johnson | 623/1.42 |
| 6,007,543 A | | 12/1999 | Ellis et al. | 606/108 |
| 6,126,673 A | | 10/2000 | Kim et al. | 606/200 |
| 6,174,326 B1 | | 1/2001 | Kitaoka et al. | 623/1 |
| 6,174,329 B1 | | 1/2001 | Callol et al. | 623/1.34 |
| 6,206,907 B1 | | 3/2001 | Marino et al. | 606/215 |
| 6,231,581 B1 | | 5/2001 | Shank et al. | 606/157 |
| 6,334,871 B1 | | 1/2002 | Dor et al. | 623/1.34 |
| 6,340,368 B1 | | 1/2002 | Verbeck | 623/1.34 |
| 6,428,462 B1 | * | 8/2002 | Mawad | 600/3 |
| 6,497,646 B1 | * | 12/2002 | Candelaria et al. | 600/7 |
| 6,641,776 B1 | * | 11/2003 | Weaver et al. | 264/642 |

FOREIGN PATENT DOCUMENTS

| | | |
|---|---|---|
| WO | 00/54704 | 9/2000 |
| WO | 02/26162 | 4/2002 |

OTHER PUBLICATIONS

U.S. Appl. No. 09/697,634, filed Oct. 26, 2000, DiCaprio.

* cited by examiner

Primary Examiner—Tan-Uyen T. Ho
(74) Attorney, Agent, or Firm—Vidas, Arrett & Steinkraus

(57) ABSTRACT

A radiopaque stent may be prepared by providing a stent preform, providing a particulate radiopaque material on at least a portion of the stent preform, pressing the particulate radiopaque material into a desired portion of the stent preform and processing the stent preform into a stent.

13 Claims, 7 Drawing Sheets

METHOD FOR ENHANCING SHEET OR TUBING METAL STENT RADIOPACITY

BACKGROUND OF THE INVENTION

Metal stents are commonly fabricated from stainless steel or nitinol sheet metal or tubing. Radiopacity of the bare metal stent is determined by the radiographic density of the stent material and the thickness of the stent wall. For small diameter stents such as coronary stents and other stents with a diameter of less than 12 mm, the bare metal stents may not necessarily have enough radiopacity for imaging purposes.

There are a number of different methods for providing and enhancing radiopacity in stents. One method of enhancing stent radiopacity involves depositing a thin surface layer of more radiographically dense material such as gold on the surface of the stent. The layer may be deposited via plating, ion deposition or any other suitable technique. Deposition methods, however, may be frustrated by poor adhesion and the resultant delamination of the deposited layer. Furthermore, the deposited layer may affect stent properties and biocompatibility adversely if it has low elongation properties or contains impurities.

Another method for providing radiopacity in stents such as wire stents is to make the stent wire of a composite construction with a radiographically dense core material such as tantalum or platinum and a casing of structural material such as stainless steel or Elgiloy.

Another method for providing a stent with radiopacity is to add an immiscible highly radiopaque agent in with the stent metal during ingot melting. With this method, however, the radiopaque constituent may be drawn out to a stringer morphology during sheet metal or tubing fabrication and become a structural weakpoint within the material.

Yet another method for providing a stent with radiopacity involves providing a radiopaque plug of material in the stent. Typically, the stent will be provided with one or more openings in which the radiopaque material is inserted.

There remains a need for novel methods of providing radiopacity in stents which do not have the adhesion problems associated with plating and which do not change the metallurgy of the base metal of the stent.

All U.S. patents and applications and all other published documents mentioned anywhere in this application are incorporated herein by reference in their entirety.

Without limiting the scope of the invention in any way, the invention is briefly summarized in some of its aspects below. Additional details of the invention and/or additional embodiments of the invention may be found in the Detailed Description of the Invention below.

A brief abstract of the some of the aspects of the technical disclosure in the specification is provided as well for the purposes of complying with 37 C.F.R. 1.72.

SUMMARY OF THE INVENTION

In one embodiment, the invention is directed to a method of preparing a stent. The method comprises the steps of providing a stent preform and providing a particulate radiopaque material on at least a portion of the stent preform. The particulate radiopaque material is pressed into a desired portion of the stent preform and the stent preform processed into a stent. The stent preform may be in the form of a sheet or a tube during the pressing step. In the former case, the stent preform may be rolled during the processing step to form a coil stent or opposing longitudinal edges may be secured one to the other to form a stent. The stent preform may be provided with a stent pattern prior to or subsequent to the pressing step.

In accordance with the invention, the processing step may include the step of heat treating the stent preform. The stent preform may be heated to a temperature above ambient temperature and less than the melting points of the stent preform and the particulate radiopaque material.

Desirably, the particulate radiopaque material is in the form of an element having an atomic weight of at least 43. Suitable particulate radiopaque materials include particulate tantalum, particulate tungsten, particulate platinum, particulate iridium, particulate gold, particulate bismuth, particulate zirconium and alloys thereof.

The particulate radiopaque material, optionally, may be coated or compounded with a diffusion activating substance such as, for example, boron. The particulate radiopaque material may be provided in a number of different forms including mixed with a binder, in the form of a dry powder, or in the form of a slurry.

Desirably, the particulate radiopaque material will be of −325 mesh or smaller. Also desirably, the particulate radiopaque material will be characterized by an average particle size of 5 microns and, more desirably, 1.5 microns or less.

The stent preform may be made of metal or polymeric material. Typically, the stent will be made of a metal such as stainless steel, Elgiloy, titanium or any of its alloys or nitinol. Other biocompatible metals may also be used.

In accordance with the invention, the pressing step may be accomplished using platens, tube drawing equipment, a rolling mill, a pressure chamber or any other suitable device for applying pressure to the stent preform. The thickness of the stent preform may remain substantially unchanged as a result of the pressing or may be decreased.

The pressing step may be repeated one or more times and, optionally, an additional quantity of the particulate radiopaque material may be placed on the stent preform in between or during the pressing steps.

Optionally, to increase bonding of the particulate radiopaque material, the stent precursor may be provided with a rough surface prior to depositing the radiopaque material. Also, the radiopaque material may be jet blasted against the stent precursor during the pressing step.

It is within the scope of the invention for a portion of the stent to be rendered radiopaque or for the entirety of the stent to be rendered radiopaque. For example, only the inner surface or the outer surface of the stent may be rendered radiopaque or only a portion of the first end of the stent and/or only a portion of the second end of the stent may be rendered radiopaque.

The invention is also directed to a medical device comprising a plurality of radiopaque regions including a first radiopaque region and a second radiopaque region, where the first and second radiopaque portions are of different radiopacities. The first and second radiopaque regions may be adjacent one another or may be separated from one another. The difference in radiopacity may be achieved by providing an amount of radiopaque material per unit area in the first region which exceeds the amount of radiopaque material provided per unit area in the second region. The difference in radiopacity may also be achieved by providing a first radiopaque material in the first region and a second radiopaque material in the second region which is of different chemical composition from the first radiopaque material.

Desirably, the medical device is a stent.

The invention is further directed to medical devices in general and stents in particular made in accordance with any of the inventive methods disclosed herein.

Additional details and/or embodiments of the invention are discussed below.

DETAILED DESCRIPTION OF THE INVENTION

Figure 1:
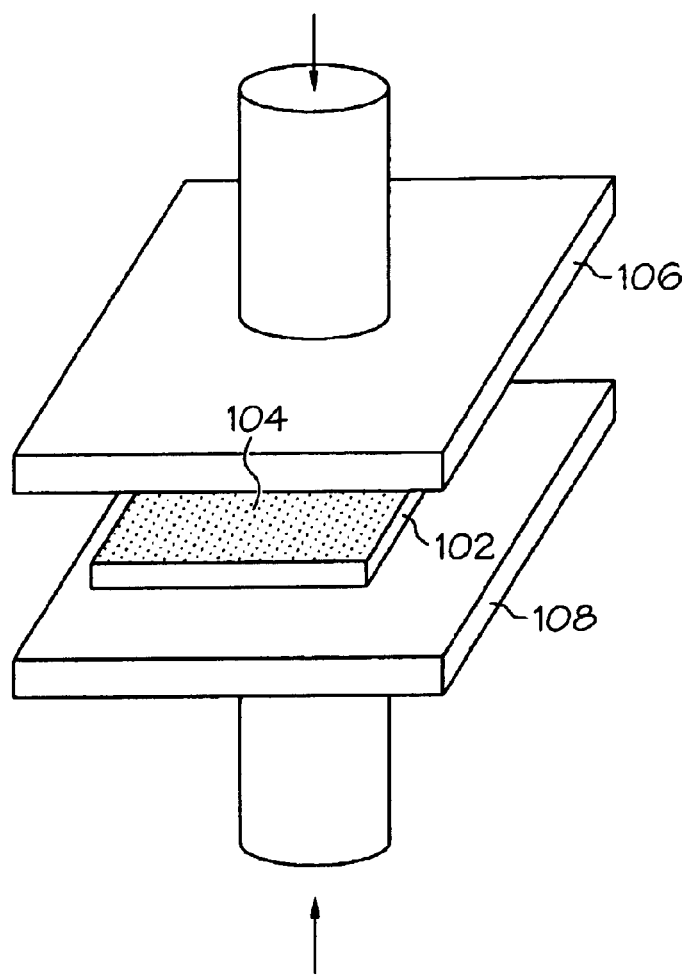
FIG. 1 is a schematic illustration of a stent precursor with particulate radiopaque material thereon immediately before being pressed between two platens.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, unless otherwise indicated, identical reference numerals used in different figures refer to the same component.

In one embodiment, the invention is directed to a method of preparing a stent comprising the steps of providing a stent preform, providing a particulate radiopaque material on at least a portion of the stent preform, pressing the particulate radiopaque material into a desired portion of the stent preform and processing the stent preform into a stent.

The stent preform may be in the form of a sheet or a tube with or without a stent pattern therein. The stent preform may be made of metal in part or in its entirety or of polymeric material in part or in its entirety. Suitable metals include stainless steel, Elgiloy, titanium or any of its alloys, nitinol and any other known stent metal. Suitable polymeric materials include certain polymeric materials, particularly engineering plastics such as thermotropic liquid crystal polymers, PTFE and bioabsorbable polymers such as Poly-L-Lactide.

As shown in FIG. 1, stent preform 102 is in the form of a sheet. Preform 102 is provided with a particulate radiopaque material 104 using any suitable technique. For example, the particulate material may be dusted onto the stent preform, poured onto the stent preform or jet blasted dry or in liquid onto the preform. Other techniques for applying the particulate radiopaque material to the stent preform include vacuum sputter deposition, and vacuum or gas plasma spray deposition.

Figure 2:
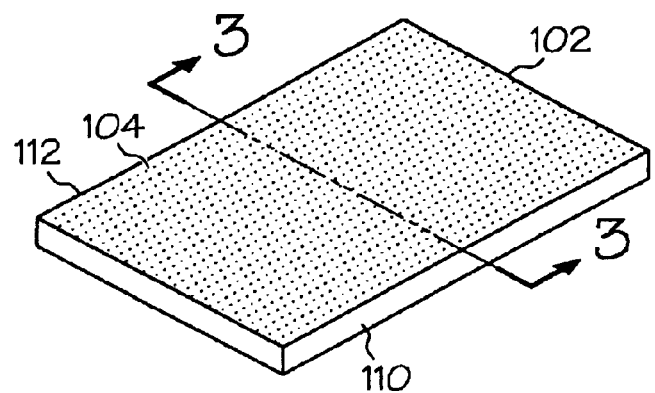
FIG. 2 is a schematic illustration of the stent precursor of FIG. 1 subsequent to being pressed.
Figure 3:
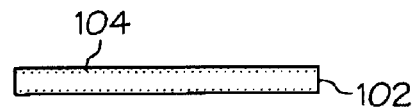
FIG. 3 is a transverse cross-sectional view of the stent precursor of FIG. 2 taken along line 3—3.

Particulate radiopaque material 104 is then pressed into stent preform using any suitable device capable of applying pressure to the stent preform. As shown in FIG. 1, stent preform 102 is disposed between a top platen 106 and a bottom platen 108 and the platens pressed together. As a result of the pressure applied to the stent preform, as shown in FIGS. 2 and 3, the radiopaque material 104 is pressed into the stent preform 102 and the stent preform rendered radiopaque. The process of adding additional radiopaque material and pressing the material into the preform optionally may be repeated as necessary until a sufficient amount of radiopaque material has been applied to the stent preform.

It is desirable to press the particulate radiopaque material into the surface of the substrate or stent precursor so that a substantial quantity of the particulate radiopaque material does not subsequently separate from the surface of the stent precursor or stent during manufacturing and use. In order to form a secure attachment of the particulate radiopaque material to the surface, the particulate radiopaque material is desirably pressed into the surface of the stent precursor by indenting or displacing the stent precursor material or by deforming the particulate radiopaque material onto the surface such that it flows into and around the topographic features of the substrate. Without being bound by theory, it is believed that as a result of the pressing operation the particulate radiopaque material is mechanically attached to the surface. High pressure and/or temperature could also be used to allow diffusion of elements between the particulate radiopaque material and the substrate forming a metallurgical bond.

In order to press the particulate radiopaque material into the surface of the substrate, sufficient pressure must be applied to the pressing platens or between the die and workpiece to deform the particulate radiopaque material or the substrate material. Desirably, the pressure that is be applied will be greater than the yield strength of the particulate radiopaque material in order for the particulate radiopaque material to be deformed onto the surface topography of the substrate. For example, the die pressure or pressure from platens to press tantalum powder into a substrate surface such as 316 alloy stainless steel will be 190 MPa (28 ksi). The room temperature yield strength of recrystallized pure tantalum metal is 190 MPa (28 ksi). The upper limit in pressure for this operation would be the ultimate tensile strength (UTS) of the substrate material to prevent fracture of it. For example, the UTS of annealed 316 alloy stainless steel strip is 485 MPa (70 ksi), so the pressing operation for tantalum powder and 316 stainless steel should be in the range of 190 to 485 MPa (28 to 70 ksi) at room temperature.

When pressing a hard particulate radiopaque material, for example, tantalum carbide or tantalum boride, into a softer substrate, for example, annealed 316 stainless steel strip, the pressure should be sufficiently high to cause the particulate radiopaque material to indent into the substrate and deform the substrate material. Desirably, the pressure will be above the yield strength of the substrate material and below the yield strength of the particulate radiopaque material. These same considerations of material properties and pressing pressures may be applied to other material systems such as, for example, pressing platinum powder onto nitinol substrate.

The pressing operation may also be performed at lower pressures by heating the materials to an elevated temperature so as to reduce the flow stresses of the materials. Desirably, the materials would be heated to a temperature less than about 150 C to avoid oxidation of the surface. Surface oxidation may reduce the effectiveness of any subsequent diffusion bonding heat treatments, because the oxide would act as a diffusion barrier between the two materials. Where it is desirable to heat the materials to higher temperatures, the pressing may be carried out in a chamber containing an inert gas (for example argon or nitrogen) or in a vacuum chamber to prevent oxidation.

Typically, in a room temperature pressing operation, pressure will be applied for a period of about 1 second to about 30 seconds. Once the necessary pressure level is reached, the material flow will be nearly instantaneous. It may prove necessary to hold the pressure application for a longer period of time where pressing temperatures in the creep regime of the materials (for slow creep flow) are used. Thus, for example, where temperatures at about ¼ to ⅓ the melting point of the particulate radiopaque material and substrate materials are used, the pressing time may range from the order of 1 minute to 3 hours or more. At pressing temperatures above about ⅓ the melting point of the materials, the pressing time required for material flow would be on the order of 1–30 seconds as the material flow would be nearly instantaneous.

The pressing step may occur at cold temperatures as low as −200 C, at ambient temperatures or at elevated temperatures of up to 100 C less than the melting point of the stent material. Thus, the pressing step may occur at temperatures as high as 1275 C for 316 stainless steel, 1200 C for nitinol, and 1568 C for titanium. Pressing at the lower end of the temperature range may, in particular, be desirable when working with nitinol in the soft martensitic phase. At low temperatures, the martensitic phase of the metal is soft and the radiopaque powder can indent more easily into the metal. On the high end, pressing at a temperature of about 100 C below the melting point of the metal is the highest temperature to which the workpiece may be heated without risking some melting. Pressing stainless steel or titanium will be easier at a high temperature because these metals are softer at higher temperatures. With metals that are easily oxidized, it is particularly desirable to press at ambient temperature to avoid oxidation of the base metal and the creation of a hard oxide surface layer. The presence of a hard oxide surface layer would not only necessitate the use of additional pressure in the pressing step but would also render it more difficult for the atoms of the powdered material, once pressed into the oxide layer, to diffuse through the oxide layer into the base metal to achieve a metallurgical bond, as discussed above.

Where a polymeric material is used for the stent precursor, the particulate radiopaque material may be heated during application so that it melts or softens the polymer to cause encapsulation of the particulate radiopaque material by the polymer.

Figure 4:
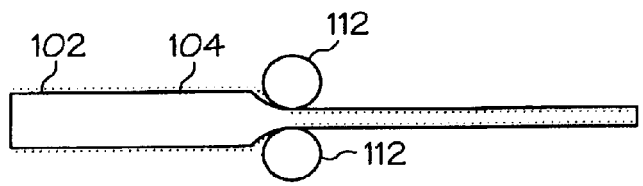
FIG. 4 is a side view of a stent precursor with particulate radiopaque material thereon as it is being drawn through a rolling mill.

The pressing may also be accomplished, as shown in FIG. 4, by applying pressure to stent preform 102 through the use of a roller 112. As shown in FIG. 4, the radiopaque material is applied prior to rolling. In another embodiment, as show in FIG. 5, particulate radiopaque material 104 may be applied to stent preform 102 during the rolling operation via applicator 113. In this way, the particulate radiopaque material is pressed into the stent preform immediately after being deposited on the preform.

Figure 5:
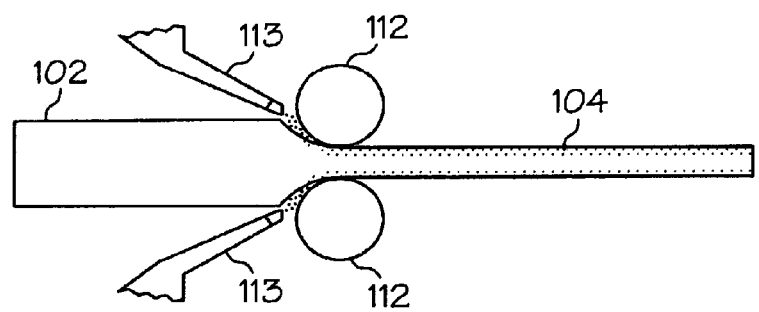
FIG. 5 is a side view of a stent precursor with particulate radiopaque material being disposed thereon immediately prior to being drawn through a rolling mill. The stent precursor is reduced in thickness as a result of being drawn through the mill.
Figure 6:
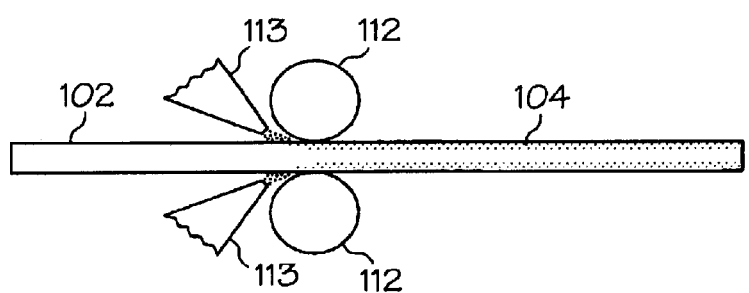
FIG. 6 is a side view similar to that of FIG. 5 differing in that the stent precursor is not substantially reduced in thickness as a result of being drawn through the rolling mill.

In the embodiment of FIG. 5, the particulate radiopaque material is pressed into the stent preform with sufficient pressure to reduce the thickness of the stent preform. It is also within the scope of the invention to use a roller without causing a substantial reduction in the thickness of the stent preform, as shown in FIG. 6.

In either case, the preform may be pressed a single time or any desirable number of times. Optionally, additional particulate radiopaque material may be added to the stent preform at any point during the process. Where multiple pressing steps are involved and additional particulate radiopaque material is added, the additional particulate radiopaque material is desirably added between pressing steps.

Yet another method for pressing the radiopaque material into the stent preform involves placing the preform in a pressure chamber and pressurizing the chamber.

It is also within the scope of the invention to combine any of the above techniques. For example, pressing of the stent with platens may be followed by the application of pressure to the stent preform with rollers.

Subsequent to pressing, any desired stent pattern may be provided in the stent preform by any suitable technique. For example, a desired stent pattern may be etched into the stent preform or may be cut into the stent preform. Chemical etching techniques, laser cutting techniques, mechanical cutting techniques or any other suitable technique may be used to provide the stent pattern in the stent preform.

Figure 7:
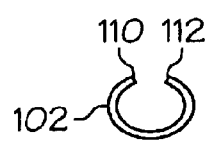
FIG. 7 is a transverse cross-sectional view of a stent precursor in the form of a sheet which is being rolled into a stent.
Figure 8:
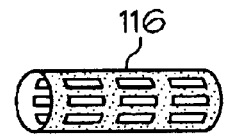
FIG. 8 is a side view of an inventive radiopaque stent formed by joining opposing edges of the stent precursor of FIG. 7.
Figure 9:
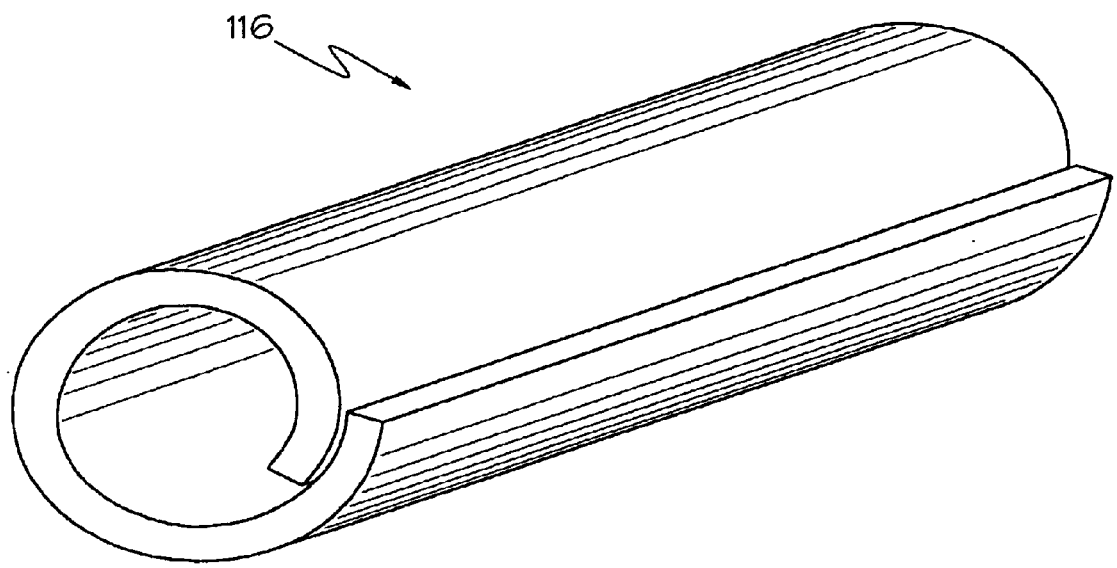
FIG. 9 is a perspective view of an inventive radiopaque coil stent.

After the desired pattern has been provided in the stent, stent preform 102 may then be rolled into a tube and opposing longitudinal edges 110 and 112 secured one to the other via any suitable technique including welding (laser or otherwise), riveting and adhesive bonding, as shown in FIG. 7, to form stent 116, as shown in FIG. 8. The stent preform may also be rolled to form a coil stent, as shown generally at 116 in FIG. 9, without securing the longitudinal edges to one another. Stent 116 as shown in FIG. 9 does not include any openings therein. The coil stent of FIG. 9 may optionally be provided with any suitable stent pattern by removing material from the stent preform.

In yet another embodiment, the stent preform may be in the form of a sheet which has already been provided with a desired stent pattern prior to pressing radiopaque material therein. Subsequent to applying and pressing the radiopaque material, the stent preform may be rolled, as described above, and the longitudinal edges optionally secured to one another.

Figure 10:
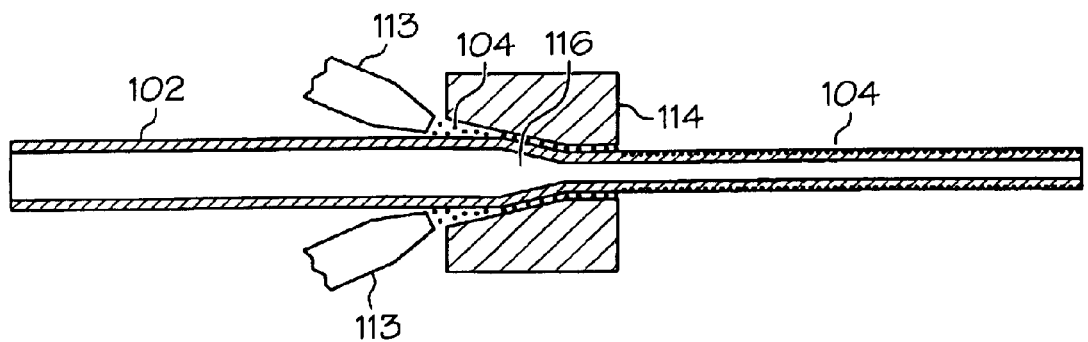
FIG. 10 is a side view illustrating a tubular stent precursor with radiopaque material disposed thereon as it is being drawn through a drawing die. The diameter of the tube is decreased as a result of being drawn.

In yet another embodiment of the invention, as shown in FIG. 10, stent preform 102 may be in the form of a tube. The tube may optionally have a stent pattern cut therein or the stent pattern may be provided subsequent to rendering the stent preform radiopaque.

Figure 11:
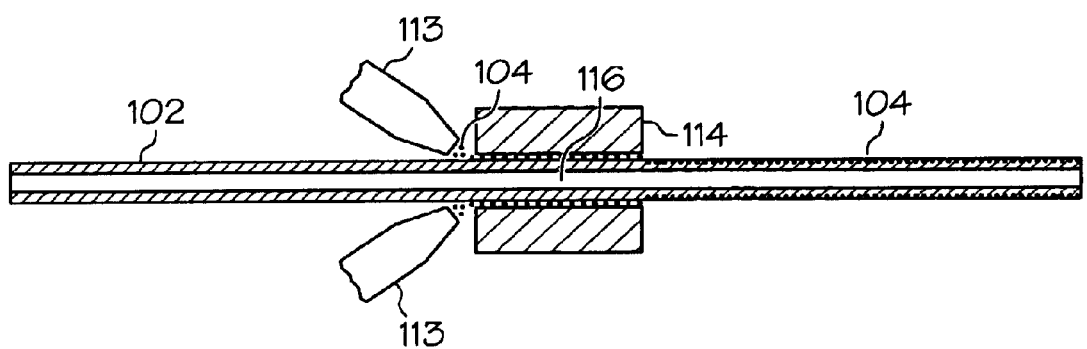
FIG. 11 is a side view illustrating a tubular stent precursor with radiopaque material disposed thereon as it is being drawn through a drawing die. The diameter of the tube is substantially unchanged as a result of being drawn.

In accordance with the invention, particulate radiopaque material is applied to the tubular stent preform and the stent preform is drawn through die 114. Desirably, the particulate radiopaque material is provided to stent preform 102 immediately before being drawn through die 114. Die 114 has an opening 116 therethrough. Opening 116 may be of non-constant diameter, as shown in FIG. 10 or may be of constant diameter, as shown in FIG. 11. In the latter case, there is substantially no reduction in the outer diameter of tubular stent preform 102. In the former case, where a die with a tapered diameter is used, the outer diameter of the stent preform is reduced as a result of being drawn through the die.

In the embodiments of FIGS. 10 and 11, the particulate radiopaque material is applied to the stent preform in the form of a slurry immediately prior to being drawn through the die.

Figure 12:
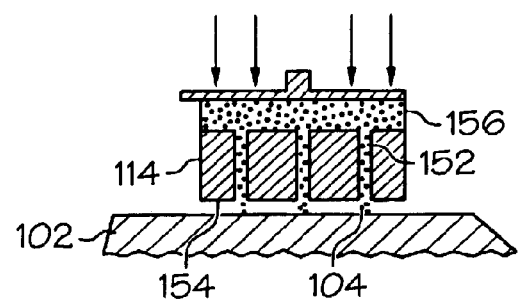
FIG. 12 is a cross-sectional view of an inventive die.

It is also within the scope of the invention to use an inventive die such as that shown at 114 in FIG. 12. Die 114 includes one or more channels 152 which terminate in openings in the inner wall surface 154 of the die. The particulate radiopaque material, desirably in the form of a slurry, may be pumped into die 114 from an outside source in communication with the one or more channels 152. The invention also contemplates the presence of optional reservoir 156 in fluid communication with the one or more channels 152.

The radiopaque material may also be pressed into the stent preform via rotary swaging in which one or more dies rotate around and impact the surface of the stent preform to press the radiopaque powder into it.

In accordance with the invention, the particulate radiopaque material may be in the form of particulate tantalum, particulate tungsten, particulate platinum, particulate iridium, particulate gold, particulate bismuth, particulate barium, particulate zirconium and alloys thereof. Examples of suitable alloys include a platinum/nickel alloy (10% nickel) and a platinum/iridium alloy (20% iridium). More generally, the particulate radiopaque material may be in the form of an elemental material having an atomic weight of at least 43 or an alloy thereof. As the atomic weight of the particulate radiopaque material is increased, the amount of the radiopaque material which is necessary to achieve the desired degree of radiopacity decreases.

Typically, the particulate radiopaque material will be applied in a layer having a thickness of 1 to 5 microns. Thinner layers may be applied when radiopaque materials with high atomic weights are used. As radiopaque materials with lower atomic weights are used, thicker layers of radiopaque material may be desirable.

Suitably, the particulate radiopaque material will be in the form of a powder of −325 mesh or smaller. More desirably, powders ranging in size from −325 mesh to −1250 mesh will be used. Most desirably, powders of approximately −625 mesh will be employed.

Typically, the particulate radiopaque material will have an average particle size of 10 microns or less. Desirably, the particulate radiopaque material will have an average particle size of 5 microns or less and more desirably, 1.5 microns or less.

Any of the above materials may be provided in powdered form. Examples of currently available powders that may be used in the present invention include −325 mesh tantalum of 99.995% purity with an average particle size of 10 microns or less available from Cerac, Inc. Milwaukee, Wisc. and −325 mesh tantalum boride of 99.5% purity with an average particle size of 10 microns or less.

The particulate radiopaque material may be provided in the form of a dry powder or may be provided in the form of a slurry. In the latter case, the slurry may be formed by mixing the particulate radiopaque material with a liquid such as water or a drawing lubricant. A soap or water soluble cutting or forming fluid lubricant may be used to suspend the particulate radiopaque material in the water or other liquid. Emulsifiable oil cutting fluids, liquid handsoap and castile soap may be used for this purpose.

Retention of the particulate radiopaque material may be further facilitated by providing the stent preform with a rough surface to entrap the radiopaque material. Desirable, the surface roughness of the stent preform will be from about 16 to 125 microinches ($R_a$). The surface may be roughened by techniques such as chemical milling, milling, laser machining, barrel finishing, grinding, grit blasting, shot peening or any other suitable technique.

The particulate radiopaque material may also be mixed with a paste or wax or other binder to temporarily bond the particulate radiopaque material to the preform prior to pressing. This would avoid having loose particles of material which detach from the stent preform and would ensure a uniform distribution of the particulate radiopaque material. The wax binder may be melted and the particulate radiopaque material blended therein. The particulate material—wax blend may then be poured, sprayed, dipped or otherwise applied to the surface of the stent preform and allowed to solidify. Suitable waxes and pastes include paraffin waxes such as Ozokerite or a Borneo type wax such as Aristowax. Ozokerite melts between 55 C and 110 C and is soluble in alcohol, benzol and naphtha. Any of these solvents may be used to remove the wax from the stent preform subsequent to pressing. Aristowax is a microcrystalline wax which melts at a temperature range between 40 C and 90 C Yet another type of wax which may be used is Ruhr wax which melts at a temperature range between 105 C and 126 C and has a low ash content (<50 ppm). These waxes may be burned off or melted off the stent preform. Desirably, the wax binder is melted or burned away from the metal after pressing so that the powder is held in place until the material is pressed. If the wax is removed prior to pressing, the powder may separate from the substrate thereby eliminating the benefit of using the wax. The particulate radiopaque material may then be pressed into the stent preform using any suitable pressing technique. Optionally, the particulate radiopaque material may be hot rolled or pressed at a temperature where the binder is vaporized. The vaporized binder may then be evacuated.

Another technique for ensuring that the particulate radiopaque material remains on the stent preform prior to pressing involves sandwiching the particulate radiopaque material between the stent preform and a layer of metal foil, wax paper or any other suitable substrate and feeding the assembly into the pressing equipment.

Optionally, the particulate radiopaque material may be coated or compounded with a diffusion activating substance, for example boron. An example of a particulate radiopaque material coated or compounded with a diffusion activating substance is tantalum boride.

Any of the inventive embodiments disclosed herein may further comprise one or more additional heat treatment steps.

The heat treatment steps may include annealing steps at higher temperatures and/or lower temperature treatment steps to allow for diffusion bonding of the particulate material to the stent preform. The latter steps are desirably carried out at a temperature above ambient temperature and less than the melting points of the stent preform and the particulate radiopaque material. Desirably, the stent preform will be heat treated subsequent to pressing the radiopaque material into the stent preform.

It is within the scope for the entirety of the resulting stent to be rendered radiopaque or for only selected portions of the resulting stent to be rendered radiopaque. As an example of the latter, the particulate radiopaque material may be provided at only the proximal and/or distal ends of the stent preform with the resulting stent being radiopaque only at the proximal and/or distal ends. As another example, where the resulting stent has sidebranch access, the stent may be rendered radiopaque in the region of sidebranch access by providing the particulate radiopaque material in the region of the stent preform corresponding to the region of sidebranch access in the finished stent. Yet another example involves selectively marking the middle of the stent preform and resulting stent.

It is also within the scope of the invention to provide the particulate radiopaque material in regions of different thickness on the stent preform so that the resulting stent has radiopaque regions of different thicknesses. The different radiopaque regions may be adjacent one another on the stent or separated by non-radiopaque portions of the stent. The variations in radiopacity may be achieved by varying the amount of the radiopaque material which is provided per unit area along one or more desired portions of the stent preform.

Providing radiopaque regions of different radiopacities may be desirable where there is a need to have portions of a stent, for example end portions, to appear clearly on a fluoroscopic image and where it is not critical if adjacent anatomy is blurred or obscured by the radiopaque region and where it is desirable to have other regions appear on a fluoroscopic image without blurring or obscuring nearby regions.

A stent having a radiopaque material of varying thickness may be provided by depositing layers of different thickness of particulate radiopaque material in different regions of the stent preform and pressing the stent preform as disclosed herein. For example, a first layer of particulate radiopaque material may be deposited in one or more desired regions of a stent preform and the preform pressed. Additional radiopaque material may then be deposited in selected regions of the stent preform and the preform pressed. The process may be repeated as necessary to build layers of radiopaque material of different thicknesses in different portions of the stent preform and ultimately, the stent.

Where an applicator is used to apply the particulate radiopaque material to the stent preform prior to rolling the preform or prior to drawing the preform through a die, the rate of delivery of the particulate radiopaque material to the stent preform may be varied to provide for layers of differing thickness of the particulate radiopaque material. The thickness of the layer of radiopaque material may also be controlled by varying the rate at which the stent preform is drawn through the rollers or through the die with the rate of delivery of particulate radiopaque material remaining constant.

The inventive methods, in many of their embodiments, allow for radiopacity to be added to a stent preform via solid state processing techniques. The radiopacity is added to a stent preform by deforming discrete particles of radiopaque material into the surface of a stent preform. This technique overcomes many of the problems associated with plating techniques and with adding radiopacity in the molten state of the stent preform.

The invention is also directed to stents made in accordance with any of the inventive methods disclosed herein.

In one embodiment, the invention is directed to a stent having an exterior surface and an interior surface where particulate radiopaque material has been pressed only into the exterior surface of the stent.

In another embodiment, the invention is directed to a stent having an exterior surface and an interior surface where particulate radiopaque material has been pressed only into the interior surface of the stent.

Figure 13:
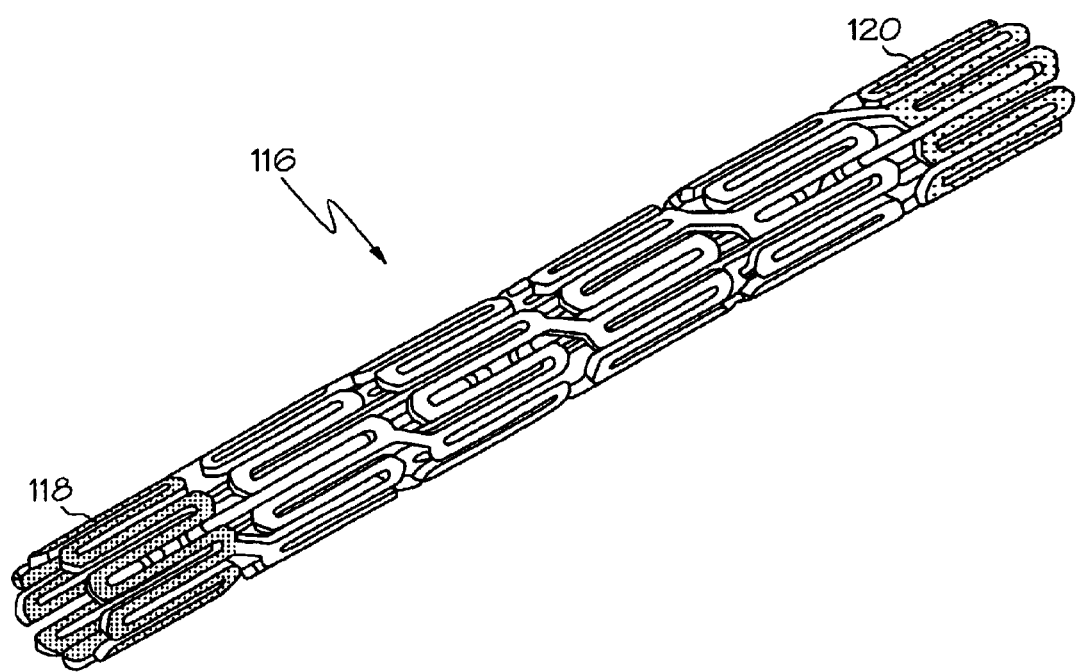
FIG. 13 is a side view of an inventive stent having radiopaque regions of different radiopacity.
Figure 14:
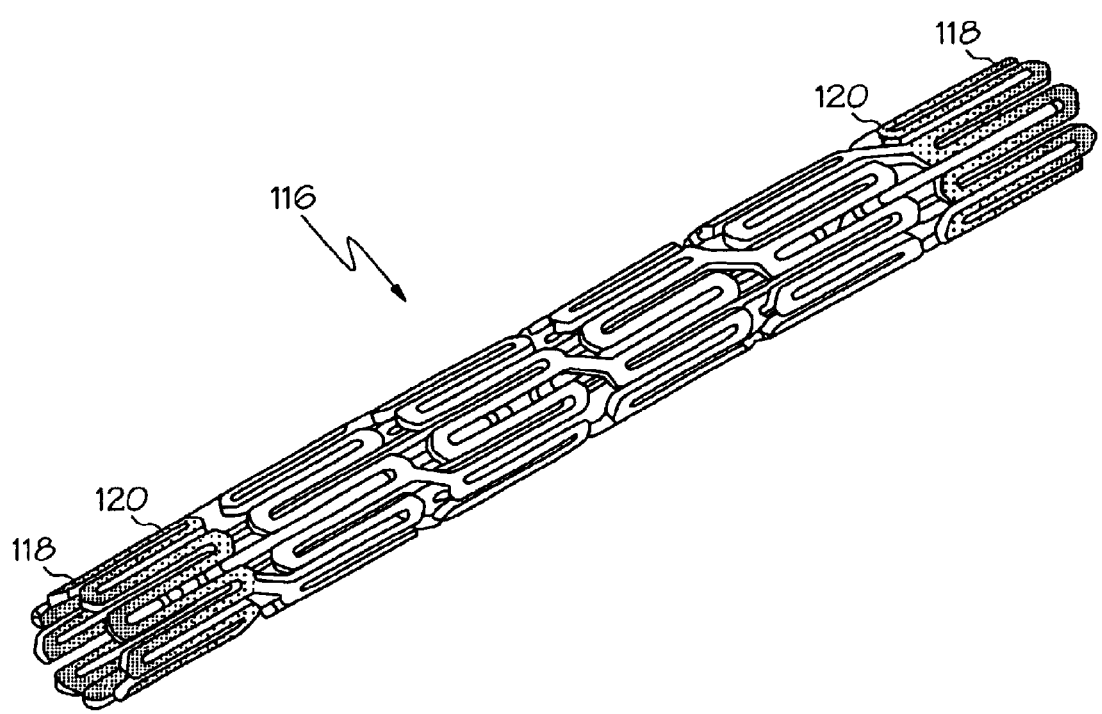
FIG. 14 is a side view of another inventive stent having radiopaque regions of different radiopacity.
Figure 15:
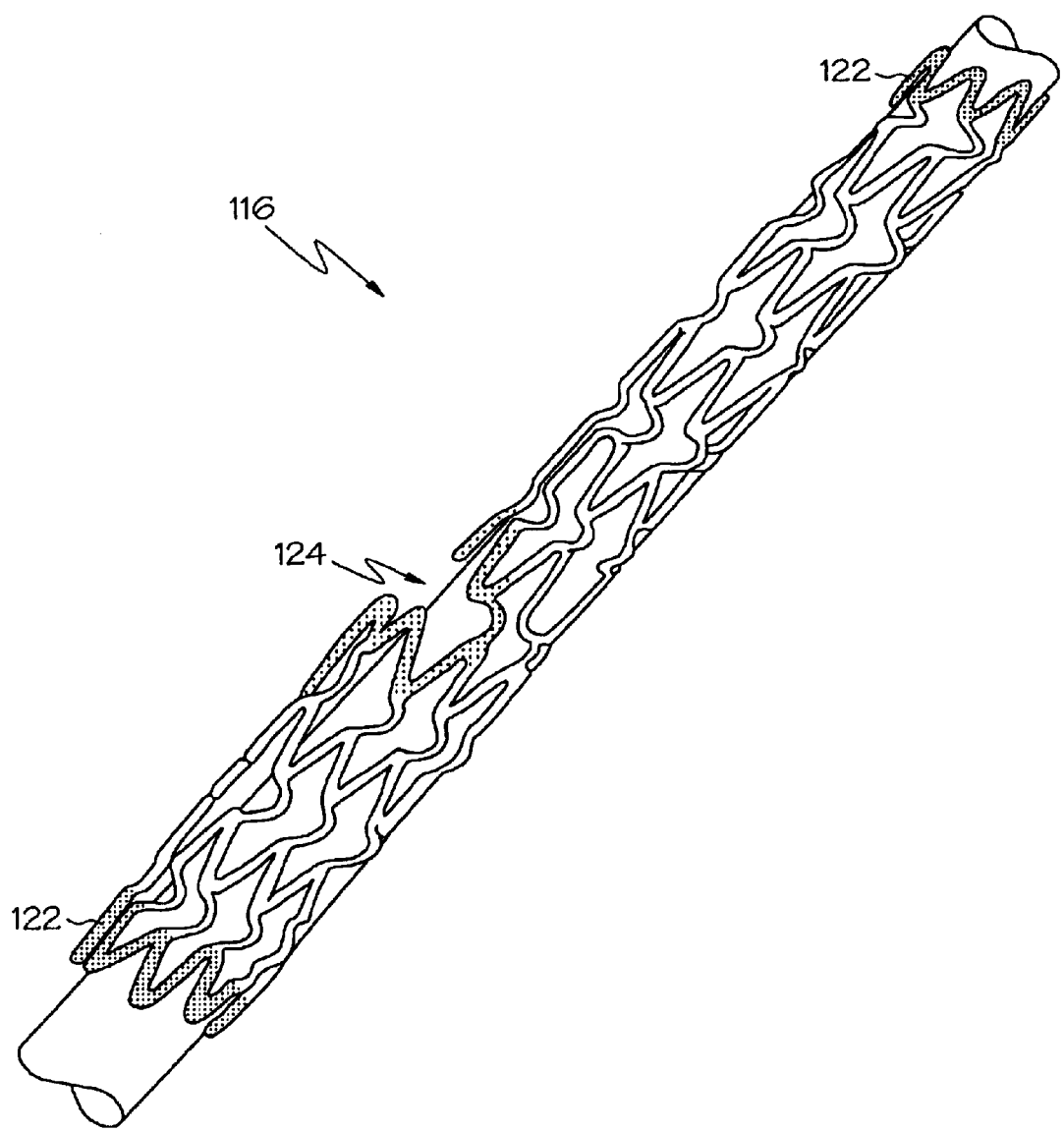
FIG. 15 is a perspective view of yet another inventive stent having radiopaque regions of different radiopacity.

In yet another embodiment, as shown in FIG. 13, the invention is directed to a stent 116 comprising a plurality of radiopaque regions including first radiopaque region 118 and second radiopaque region 120. The first and second radiopaque portions are of different radiopacities. First radiopaque region 118 is more radiopaque than second radiopaque region 120 as indicated by the difference in shading in the figure. In the stent of FIG. 13, the first and second radiopaque regions do not abut one another. The stent may also be provided in embodiments in which the first and second radiopaque regions are adjacent one. The radiopacity of the stent may taper over a given portion of the stent or may change abruptly. For example, as shown in FIG. 14, the amount of radiopaque material may gradually decrease from a maximum amount at the ends of the stent in region 118 to a decreased radiopacity in region 120 as indicated by the difference in shading in the figure. The remainder of the stent is not radiopaque. As shown in FIG. 15, ends 122 of stent 116 may be provided with a first amount of radiopaque material and a region of sidebranch access 124 may be provided with sufficient radiopaque material to be viewable in a fluoroscopic image but with less radiopaque material than is present in the ends of the stent, as indicated by the shading in the figure, to avoid blurring or obscuring areas of the stent adjacent the region of sidebranch access.

The variable radiopacity may be achieved by varying the amount of radiopaque material per unit area in desired portions of the stent. The variable radiopacity may also be achieved by varying the radiopaque material that is applied to the stent. For example, one region of the stent may comprise a first radiopaque material of a first atomic weight and another region of the stent may comprise a second radiopaque material of a second atomic weight different from the first atomic weight.

In addition to being directed to stents and methods of forming stents, the invention is directed more generally to methods of forming medical devices exhibiting radiopacity. Desirably, the medical devices are implantable in the body, as in the case of stents. Other medical devices which may be provided in accordance with the inventive methods disclosed herein include vena cava filters, occlusion devices, device anchors, catheters and stent mounting hubs. An example of a vena cava filter is disclosed in U.S. Pat. No. 6,126,673. An example of an occlusion device is disclosed in U.S. Pat. No. 6,206,907. An example of a device anchor is disclosed in U.S. Pat. No. 6,231,581. An example of a catheter and hubs is disclosed in U.S. Pat. No. 6,007,543.

EXAMPLE

Annealed 316L stainless steel tubing having an outer diameter of 0.25 inches and a wall thickness of 0.01 inches may be drawn so that the outer diameter is reduced to 0.20 inches with the wall thickness remaining approximately 0.01 inches thick. A slurry comprising particulate radiopaque material may be applied to the tubing to coat the tubing and the tubing drawn to an outer diameter of 0.15 inches and a wall thickness of 0.007 inches. Desirably, the die has an entrance angle such that the coating is not skived off, but is instead pressed into the surface of the tubing within the die (as shown, for example, in FIG. 10). Additional slurry comprising the particulate radiopaque material may be applied to the tube and the tubing drawn to an outer diameter of 0.125 inches and a wall thickness of 0.005 inches. Next, the tubing is heated to 125 C to evaporate the slurry from the surface of the tubing. The tubing is then annealed at 1100 C for 20 minutes in an inert gas or in hydrogen gas to soften the tube and facilitate diffusion bonding between the particulate radiopaque material and the stainless steel tubing. The tubing may be drawn down further in several steps to an outer diameter of 0.100 inches, 0.075 inches and finally to an outer diameter of 0.060 inches. The drawn tubing may then be annealed at 1025 C for 5 minutes in an inert gas or hydrogen gas for a final recrystallization. A desired stent pattern may then be laser cut into the tubing and the surface of the tubing polished or otherwise finished resulting in a stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 5 may be taken as alternatively dependent on claim 4, claim 2 or claim 1, claim 6 may be taken as alternatively dependent from claim 4, claim 2 or claim 1; etc.).

What is claimed is:

1. An implantable medical device having a non-porous surface comprising a plurality of radiopaque regions, said plurality of radiopaque regions comprising a layer of particulate radiopaque material which is pressed into the surface such that the particulate radiopaque material is embedded in the surface and mechanically attached to said surface, and said implantable medical device including a first radiopaque region and a second radiopaque region, the first and second radiopaque regions of different radiopacities.

2. The implantable medical device of claim 1 in the form of a stent.

3. The implantable medical device of claim 2 wherein the first and second radiopaque regions are adjacent one another.

4. The implantable medical device of claim 2 wherein the first and second radiopaque regions do not abut one another.

5. The implantable medical device of claim 2 wherein the amount of radiopaque material per unit area in the first region exceeds the amount of radiopaque material per unit area in the second region.

6. The implantable medical device of claim 2 wherein the first radiopaque region comprises a first radiopaque material and the second radiopaque region comprises a second radiopaque material of a different chemical composition from the first radiopaque material.

7. The stent of claim 1 wherein said particulate radiopaque material has an average particle size of 5 microns or less.

8. The stent of claim 1 wherein said particulate radiopaque material has an average particle size of 1.5 microns or less.

9. The stent of claim 1 wherein said particulate radiopaque material is −325 mesh or less.

10. The stent of claim 1 wherein said particulate radiopaque material is in the form of an element having an atomic weight of at least 43.

11. The stent of claim 1 wherein said particulate radiopaque material comprises at least one member selected from the group consisting of particulate tantalum, particulate tungsten, particulate platinum, particulate indium, particulate gold, particulate bismuth, particulate zirconium, alloys thereof and mixtures thereof.

12. The stent of claim 1 wherein said radiopaque regions formed by applying at least one of a particulate radiopaque material which has been compounded with a diffusion activating substance, a particulate radiopaque material which has been mixed with a binder, a particulate radiopaque material in the form of a powder, a particulate radiopaque material mixed as a slurry.

13. The stent of claim 12 wherein said diffusion activating substance is boron.

* * * * *